US009644174B2

(12) United States Patent
Miravet Celades et al.

(10) Patent No.: US 9,644,174 B2
(45) Date of Patent: May 9, 2017

(54) ENCAPSULATES

(75) Inventors: Juan Felipe Miravet Celades, Castellon (ES); Beatriu Escuder Gil, Sant Mateu-Castellon (ES); Vincent Josep Nebot-Carda, Castellon (ES); Johan Smets, Lubbeek (BE); Susana Fernandez Prieto, Benicarlo (ES)

(73) Assignee: The Procter & Gamble Company, Cincinnati, OH (US)

( * ) Notice: Subject to any disclaimer, the term of this patent is extended or adjusted under 35 U.S.C. 154(b) by 988 days.

(21) Appl. No.: 13/612,994

(22) Filed: Sep. 13, 2012

(65) Prior Publication Data
US 2013/0061883 A1 Mar. 14, 2013

Related U.S. Application Data

(60) Provisional application No. 61/533,989, filed on Sep. 13, 2011.

(51) Int. Cl.
| *C11D 3/39* | (2006.01) |
| *A61K 8/38* | (2006.01) |
| *A61K 8/11* | (2006.01) |
| *C11D 11/00* | (2006.01) |
| *C11D 17/00* | (2006.01) |
| *B01J 13/04* | (2006.01) |
| *A61K 8/41* | (2006.01) |
| *A61K 8/42* | (2006.01) |
| *A61K 8/60* | (2006.01) |
| *A61Q 5/08* | (2006.01) |
| *A61K 8/73* | (2006.01) |
| *A61K 8/81* | (2006.01) |

(52) U.S. Cl.
CPC ............. *C11D 3/3935* (2013.01); *A61K 8/11* (2013.01); *A61K 8/38* (2013.01); *A61K 8/41* (2013.01); *A61K 8/42* (2013.01); *A61K 8/60* (2013.01); *A61K 8/731* (2013.01); *A61K 8/8129* (2013.01); *A61Q 5/08* (2013.01); *B01J 13/043* (2013.01); *C11D 3/394* (2013.01); *C11D 11/0082* (2013.01); *C11D 17/0039* (2013.01)

(58) Field of Classification Search
CPC .... C11D 17/039; C11D 3/3935; C11D 17/003
See application file for complete search history.

(56) References Cited

U.S. PATENT DOCUMENTS

| 5,846,922 | A | 12/1998 | Lagnemo et al. | |
| 7,893,014 | B2 * | 2/2011 | van Buskirk | C11D 3/0015 510/327 |
| 7,910,535 | B2 * | 3/2011 | Panandiker | C11D 3/40 510/296 |
| 8,168,579 | B2 * | 5/2012 | Fernandez Prieto | C07C 237/22 510/303 |
| 8,222,197 | B2 * | 7/2012 | Fernandez Prieto | C07C 237/22 510/303 |
| 8,236,745 | B2 * | 8/2012 | Panandiker | C11D 3/40 510/276 |
| 8,633,148 | B2 * | 1/2014 | Smets | C11D 3/373 510/302 |
| 9,243,215 | B2 | 1/2016 | Dihora et al. | |
| 2006/0172909 | A1 | 8/2006 | Schmiedel et al. | |
| 2008/0229519 | A1 * | 9/2008 | Depoot | C11D 3/227 8/401 |
| 2009/0069207 | A1 * | 3/2009 | Panandiker | C11D 3/40 510/296 |
| 2009/0088363 | A1 * | 4/2009 | Panandiker | C11D 3/40 510/343 |
| 2011/0021408 | A1 * | 1/2011 | Meek | C11D 3/226 510/321 |
| 2011/0220536 | A1 * | 9/2011 | Fernandez-Prieto | C07C 237/22 206/524.7 |
| 2011/0220537 | A1 * | 9/2011 | Fernandez-Prieto | C07C 237/22 206/524.7 |
| 2011/0245134 | A1 * | 10/2011 | Smets | C11D 3/373 510/375 |
| 2011/0245136 | A1 * | 10/2011 | Smets | B01J 13/02 510/513 |
| 2012/0017947 | A1 * | 1/2012 | Fernandez Prieto | C11D 3/38672 134/26 |
| 2012/0028874 | A1 * | 2/2012 | Fernandez Prieto | C11D 3/222 510/375 |

FOREIGN PATENT DOCUMENTS

WO WO 2008/102127 A2 8/2008

OTHER PUBLICATIONS

International Search Report for International Application No. PCT/US2012/054968, mailed Jan. 31, 2013, 16 pages.

* cited by examiner

*Primary Examiner* — Gregory Webb
(74) *Attorney, Agent, or Firm* — Gregory S. Darley-Emerson; Leonard W. Lewis; Steven W. Miller

(57) ABSTRACT

The present application relates to encapsulated, preformed peracids and products comprising such encapsulates, as well as processes for making and using such encapsulates and products comprising such encapsulates. Such products deliver bleaching that results in superior whiteness and stain removal without the stability issues that are normally associated with certain bleaching systems.

18 Claims, No Drawings

ENCAPSULATES

CROSS REFERENCE TO RELATED APPLICATION

This application claims priority to U.S. Provisional Application Ser. No. 61/533,989, filed Sep. 13, 2011.

FIELD OF INVENTION

The present application relates to encapsulated, preformed peracids and products comprising such encapsulates, as well as processes for making and using such encapsulates and products comprising such encapsulates.

BACKGROUND OF THE INVENTION

Products, for example, consumer products may comprise one or more benefit agents that can provide a desired benefit to such product and/or a situs that is contacted with such a product—for example stain removal and/or bleaching. Unfortunately, in certain products, for example, fluid products, benefit agents such as preformed peracids may be degraded by or degrade components of such products before such product is used—this is particularly true when the product has a pH greater than about 6. Thus, a protection system that protects the components of a product from a benefit agent is desired. Efforts have been made in this area but typically either fail to provide the required level of protection or fail to release the benefit agent when it is needed. Thus, the need for encapsulated benefit agents that are available during product use, yet which do not damage such product during product storage, remains. Applicants disclose a particle comprising a benefit agent, such as a preformed peracid, wherein the benefit agent is contained in a hydrogel core, said core having a pH wherein the benefit agent is stable. Such core is then encapsulated by an encapsulating material. While not being bound by theory, Applicants believe that said core's environment is such that the benefit agent is stable while the encapsulating material allows for a separate environment outside of the particle, for example a pH greater than 6. Surprisingly, the difference in the core's environment and the environment outside of the particle can be so dramatically different that materials that could not previously be combined in a composition may now be combined with minimal stability issues. Yet, during use the benefit agent is, as desired, released. Thus, multiple benefits can now be obtained from a single composition, for example, bleaching and enzymatic cleaning can now be obtained from liquid detergent products.

SUMMARY OF THE INVENTION

The present application relates to particles comprising a benefit agent encapsulated by a first layer that is in turn encapsulated by a second material, and products comprising such particles, as well as processes for making and using such particles and products comprising such particles.

DETAILED DESCRIPTION OF THE INVENTION

Definitions

As used herein "consumer product" means baby care, beauty care, fabric & home care, family care, feminine care, health care, or devices generally intended to be used in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshing), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/ or freshing), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshing that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Composition

In one aspect a composition having a pH of from about 6.5 to about 14, from about 7 to about 10 or even from about 7.5 to about 9, said composition comprising an encapsulate having a diameter of from about 10 microns to about 450 microns, from about 20 microns to about 350 microns, or even from about 35 microns to about 250 microns, said encapsulate comprising a shell and a matrix composition, said shell encapsulating said matrix composition, said matrix composition having a pH from about 3.5 to about 6, or even 4.5 to about 5.5, said matrix composition comprising a matrix network material and matrix benefit agent cores, said matrix benefit agent cores being entrapped in said matrix network material is disclosed.

In one aspect of said composition, said matrix composition may comprise a self-assembled matrix network material having a molecular weight from about 150 g/mol to about 1500 g/mol, from about 250 g/mol to about 1200 g/mol, or even from about 500 g/mol to about 850 g/mol.

In one aspect of said composition, said self-assembled matrix network material may comprise a pH tuneable di-amido gellant. pH tuneable di-amido gellants may provide the fluid composition with a viscosity profile that is dependent on the pH of the composition. Hence, the pH tuneable di-amido gellant may be added to a fluid composition at a pH at which the viscosity is sufficiently low to allow easy mixing. The pH tuneable di-amido gellants may comprise at least one pH sensitive group. When a pH tuneable di-amido gellant is added to a fluid composition comprising a polar protic solvent such as water, it is believed that the nonionic species form the viscosity building network while the ionic species are soluble and do not form a viscosity building network. By increasing or decreasing the pH (depending on the selection of the pH-sensitive groups) the amido gellant may be either protonated or deprotonated. Thus, by changing the pH of the solution, the solubility, and hence the viscosity building behaviour, of the di-amido gellant can be controlled. By careful selection of the pH-sensitive groups, the pKa of the amido gellant can be tailored. Hence, the choice of the pH-sensitive groups can be used to select the pH at which the di-amido gellant builds viscosity.

In one aspect of said composition, said self-assembled matrix network material is in its neutral viscosity building form at a pH of from about 3 to about 6.

In one aspect of said composition, said matrix network material may have a pKa of from about 1 to about 14, from about 2 to about 9, from about 3 to about 6, or even from about 4.5 to about 5.5.

In one aspect of said composition, said matrix composition may comprise, based on total matrix composition weight, from 0.01 wt % to 10 wt % of a matrix network material having a formula:

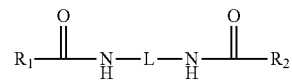

wherein $R_1$ and $R_2$ are aminofunctional end-groups; L is a backbone moiety having molecular weight from 14 to 500 g/mol; and at least one of L, $R_1$ or $R_2$ may comprise a pH-sensitive group.

In one aspect of said matrix network material, said $R_1$ and $R_2$ end-groups may comprise amidofunctional end groups.

In one aspect of said composition, said matrix network material may comprise at least one amido functional group, and further may comprise at least one pH-sensitive group. In one aspect, the matrix network material may have a molecular weight from about 150 to about 1500 g/mol, from about 300 g/mol to about 900 g/mol, or even from about 400 g/mol to about 700 g/mol.

In one aspect, L has the formula:

$$L = A_a\text{-}B_b\text{-}C_c\text{-}D_d,\qquad\text{[III]}$$

wherein: (a+b+c+d) is from 1 to 20; and A, B, C and D are independently selected from the linking groups consisting of:

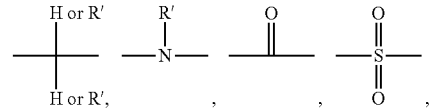

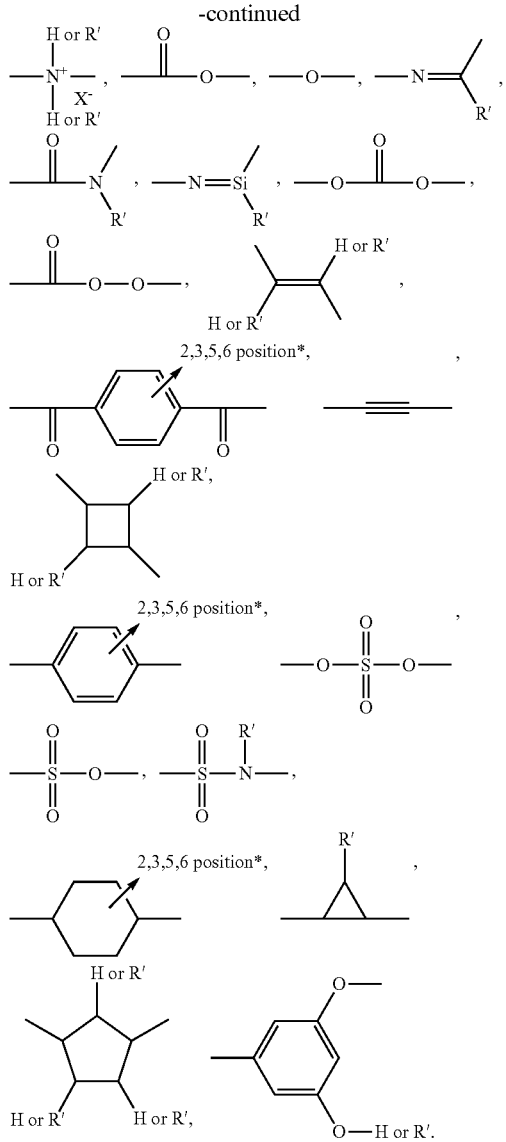

In one aspect, L is selected from $C_2$ to $C_{20}$ hydrocarbyl chains, from $C_6$ to $C_{12}$, or even from $C_8$ to $C_{10}$.

In one aspect, $R_1$ is $R_3$ or

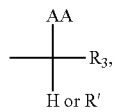

$R_2$ is $R_4$ or

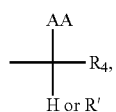

wherein each AA is independently selected from the group consisting of:

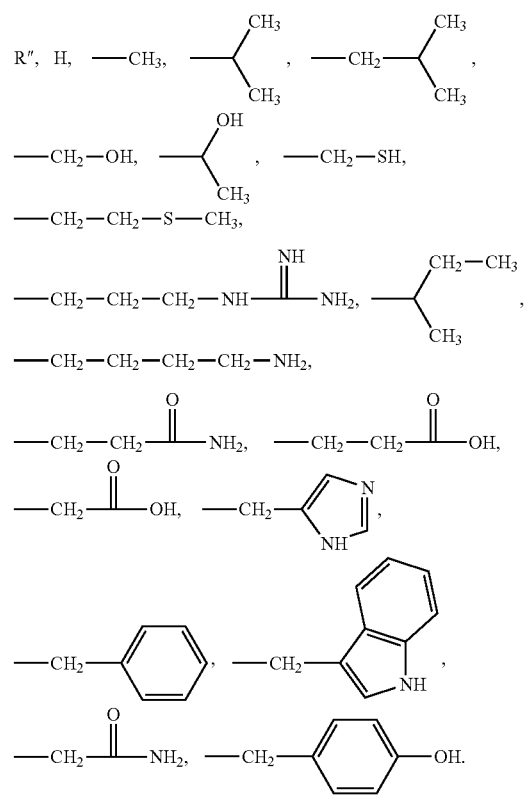

and $R_3$ and $R_4$ independently have the formula:

$$(L')_o\text{-}(L'')_q\text{—}R, \qquad [IV]$$

wherein: (o+q) is from 1 to 10; L' and L" are linking groups, independently selected from the same groups as A, B, C and D in equation [III]; and R, R' and R" are independently selected either from the same group as AA, either from the pH-sensitive-groups consisting of:

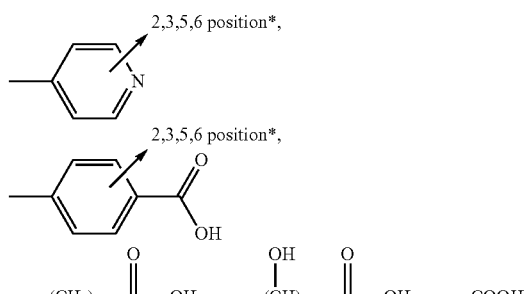

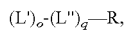

*the arrow indicates up to 4 substitutions in the positions indicated, n and m are integers from 1 to 20 or from the non-pH-sensitive groups consisting of:

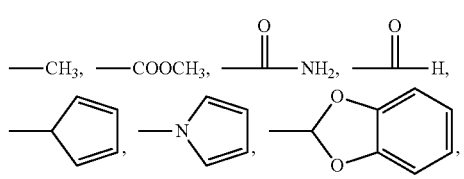

-continued

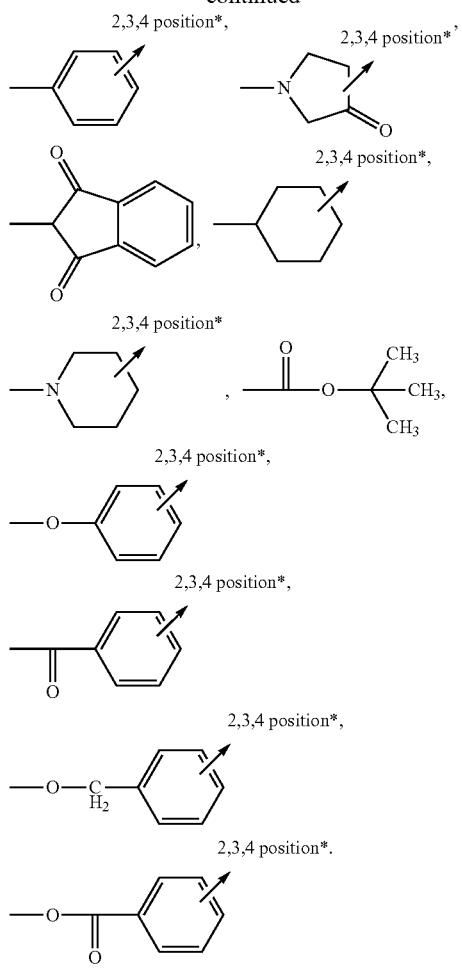

such that at least one of L, R, R' and R" comprises at least one pH-sensitive group. In one aspect, R may comprise the pH-sensitive group.

In one aspect, the matrix network material having structure [I] is characterized in that: L is an aliphatic linking group with a backbone chain of from 2 to 20 carbon atoms, in one aspect, L may be —(CH$_2$)$_n$— wherein n is selected from 2 to 20, and both R$_1$ and R$_2$ have the structure:

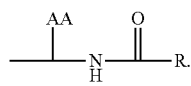

in one aspect, AA is selected from the group consisting of:

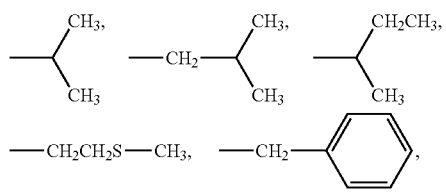

and R is selected from the pH-sensitive groups consisting of:

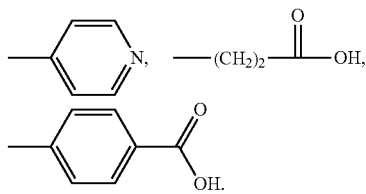

In another aspect, two or more of L, L' and L" are the same group.

The matrix network material described in formula [I] can be symmetric with respect to the L entity or can be asymmetric. Without intending to be bound by theory, it is believed that symmetric matrix network materials allow for more orderly structured networks to form, whereas compositions comprising one or more asymmetric matrix network materials can create disordered networks.

Suitable matrix network materials having structure [I] may be selected from table 1. In one aspect of both types of pH tuneable amido gellant structures, AA may comprise at least one of: Alanine, β-Alanine and substituted Alanines; Linear Amino-Alkyl Carboxylic Acid; Cyclic Amino-Alkyl Carboxylic Acid; Aminobenzoic Acid Derivatives; Aminobutyric Acid Derivatives; Arginine and Homologues; Asparagine; Aspartic Acid; p-Benzoyl-Phenylalanine; Biphenylalanine; Citrulline; Cyclopropylalanine; Cyclopentylalanine; Cyclohexylalanine; Cysteine, Cystine and Derivatives; Diaminobutyric Acid Derivatives; Diaminopropionic Acid; Glutamic Acid Derivatives; Glutamine; Glycine; Substituted Glycines; Histidine; Homoserine; Indole Derivatives; Isoleucine; Leucine and Derivatives; Lysine; Methionine; Naphthylalanine; Norleucine; Norvaline; Ornithine; Phenylalanine; Ring-Substituted Phenylalanines; Phenylglycine; Pipecolic Acid, Nipecotic Acid and Isonipecotic Acid; Proline; Hydroxyproline; Thiazolidine; Pyridylalanine; Serine; Statine and Analogues; Threonine; Tetrahydronorharman-3-carboxylic Acid; 1,2,3,4-Tetrahydroisoquinoline; Tryptophane; Tyrosine; Valine; and combinations thereof.

In one aspect, said matrix network material may have a minimum gelling concentration (MGC) of from 0.1 to 100 mg/mL, from 0.1 to 25 mg/mL, or even from 0.5 to 10 mg/mL in water, at the target pH of the matrix composition, in accordance with the MGC Test Method. The MGC as used herein can be represented as mg/ml or as a wt %, where wt % is calculated as the MGC in mg/ml divided by 10.

In one aspect of said composition, said matrix composition may comprise a buffer and/or buffer precursor, in one aspect, said buffer may comprise δ-gluconic acid and said buffer precursor may comprise gluco-δ-lactone.

In one aspect of said composition, said shell may comprise a material selected from the group consisting of
a) a material comprising polyvinyl pyrrolidone, in one aspect, such material may comprise polyvinyl pyrrolidone, polyvinyl pyrrolidone styrene copolymers, polyvinyl pyrrolidone vinyl acetate copolymers, polyvinyl pyrrolidone imidazole copolymers and mixtures thereof;
b) polymers derived from hydrophilic monomers comprising diamines, triamines, diols and mixtures thereof. In one aspect, such diamines and triamines may comprise diethylene triamine, hexamethylene diamine, ethylene diamine and mixtures thereof. In one aspect, such diol may comprise ethylene glycol, 1,2-propanediol, 1,3-propanediol, 1-propen-1,3-diol, 1,4-butanediol, 1,3-butanodiol, 1,2-butanediol, 3-butene-1,2-diol, 3-butene-1,4-diol, 1,5-pentanediol, 1-penten-1,5-diol, 1,6-hexanediol, 3,4-dihydroxy-3-cyclobutene-1,2-dione, 5-hydroxy-2-(hydroxymethyl)-4H-pyran-4-one, (2E)-2,3-dihydroxy-2-butenedioic acid hydrate, 2,3,5,6-tetrahydroxybenzo-1,4-quinone, 4,4-dimethyl-1,2-cyclopentanediol, 3-methyl-1,3,5-pentanetriol, 3-methyl-1,5-pentanediol, (1S,2S)-1,2-cyclopentanediol, 1,3-cyclohexanediol, 1,5-hexanediol, 1,2,6-hexanetriol, 1,2,4-butanetriol and mixtures thereof.

c) polymers derived from hydrophobic monomers comprising di- and/or tri-acyl chlorides, diisocyanates, bis-chloroformates and mixtures thereof. In one aspect, such di- and/or tri-acyl chlorides may comprise trimesoyl chloride, teraphthaloyl chloride, and mixtures thereof. In one aspect, such diisocyanate may comprise 1-isocianato-4-[(4-fenilisocianato)metil]benzene, 2,4-diisocyanato-1-methyl-benzene, 1,6-diisocyanato-hexane, 5-isocyanato-1-(isocyanatomethyl)-1,3,3-trimethyl-cyclohexane and mixtures thereof. In one aspect, such bischloroformates may comprise bisphenol A bis(chloroformate), bisphenol Z bis(chloroformate) and mixtures thereof.

d) a material comprising a polyvinyl alcohol derivative, in one aspect such material may comprise polyvinyl alcohol, polyvinyl acetate, polyvinyl alcohol 2-acrylamide-2-methylpropane sulfonate copolymers, copolymers of polyvinyl alcohol derived from monomers comprising primary and secondary amine, polyvinyl alcohol imidazoles copolymers and mixtures thereof; in another aspect such material may be cross-linked with gluteraldehyde, sodium tetraborate, ethyl acetate and mixtures thereof. In one aspect, the material comprises a mixture of a polyvinyl alcohol derivative and a cross-linked polyvinyl alcohol derivative.

e) a material comprising a polymer with a cloud point from about 0° C. to about 120° C., or even from about 20° C. to about 60° C., in one aspect, such material may comprise poly-(N-isopropylacrylamide), poly-(vinyl alcohol-co-vinyl acetate), poly-(acrylamide-co-diacetoneacrylamide) or ethyl cellulose.

f) a material comprising a cellulosic polymer, in one aspect such material may comprise starch, cellulose acetate, cellulose acetate phthalate, hydroxylpropyl methyl cellulose, methyl cellulose, ethyl cellulose, hydroxypropyl methylcellulose phthalate and mixtures thereof, in one aspect such starch may comprise a octenyl succinated starch, a hydroxyethylated starch, a hydroxypropylated starch and mixtures thereof.

g) a material comprising a wax, in one aspect such wax having a melting point from about 35° C. to about 75° C.

h) a material comprising a non-cellulosic, natural polymer, in one aspect such material may comprise shellac, zein and mixtures thereof;

and said matrix benefit agent cores may comprise a material selected from the group consisting of a preformed peracid, a metal catalyst, a bleach activator, a bleach booster and a diacyl peroxide.

In one aspect of said composition, a) said metal catalyst may comprise a material selected from the group consisting of dichloro-1,4-diethyl-1,4,8,11-tetraaazabicyclo[6.6.2]hexadecane manganese (II); dichloro-1,4-dimethyl-1,4,8,11-tetraaazabicyclo[6.6.2]hexadecane manganese(II) and mixtures thereof;

b) said bleach booster may comprise material selected from the group consisting of 2-[3-[(2-hexyldodecyl)oxy]-2-(sulfooxy)propyl]-3,4-dihydroisoquinolinium, inner salt; 3,4-dihydro-2-[3-[(2-pentylundecyl)oxy]-2-(sulfooxy)propyl]isoquinolinium, inner salt; 2-[3-[(2-butyldecyl)oxy]-2-(sulfooxy)propyl]-3,4-dihydroiso-quinolinium, inner salt; 3,4-dihydro-2-[3-(octadecyloxy)-2-(sulfooxy)propyl]isoquinolinium, inner salt; 2-[3-(hexadecyloxy)-2-(sulfooxy)propyl]-3,4-dihydroisoquinolinium, inner salt; 3,4-dihydro-2-[2-(sulfooxy)-3-(tetradecyloxy)propyl]isoquinolinium, inner salt; 2-[3-(dodecyloxy)-2-(sulfooxy)propyl]-3,4-dihydroisoquinolinium, inner salt; 2-[3-[(3-hexyldecyl)oxy]-2-(sulfooxy)propyl]-3,4-dihydroisoquinolinium, inner salt; 3,4-dihydro-2-[3-[(2-pentylnonyl)oxy]-2-(sulfooxy)propyl]isoquinolinium, inner salt; 3,4-dihydro-2-[3-[(2-propylheptyl)oxy]-2-(sulfooxy)propyl]isoquinolinium, inner salt; 2-[3-[(2-butyloctyl)oxy]-2-(sulfooxy)propyl]-3,4-dihydroisoquinolinium, inner salt; 2-[3-(decyloxy)-2-(sulfooxy)propyl]-3,4-dihydroisoquinolinium, inner salt; 3,4-dihydro-2-[3-(octyloxy)-2-(sulfooxy)propyl]isoquinolinium, inner salt; 2-[3-[(2-ethylhexyl)oxy]-2-(sulfooxy)propyl]-3,4-dihydroisoquinolinium, inner salt and mixtures thereof;

c) said bleach activator may comprise a material selected from the group consisting of tetraacetyl ethylene diamine (TAED); benzoylcaprolactam (BzCL); 4-nitrobenzoylcaprolactam; 3-chlorobenzoyl¬caprolactam; benzoyloxybenzenesulphonate (BOBS); nonanoyloxybenzene¬sulphonate (NOBS); phenyl benzoate (PhBz); decanoyloxybenzoic acid (DOBA); (6-octanamidocaproyl)oxybenzenesulfonate; (6-nonanamidocaproyl) oxybenzenesulfonate; (6-decanamidocaproyl)oxybenzenesulfonate and mixtures thereof;

d) said preformed peracid may comprise a material selected from the group consisting of peroxymonosulfuric acids; perimidic acids; percabonic acids; percarboxilic acids and salts of said acids; in one aspect said percarboxilic acids and salts thereof may be phthalimidoperoxyhexanoic acid, 1,12-diperoxydodecanedioic acid; or monoperoxyphthalic acid (magnesium salt hexahydrate); amidoperoxyacids, in one aspect, said amidoperoxyacids may be N,N'-terephthaloyl-di(6-aminocaproic acid), a monononylamide of either peroxysuccinic acid (NAPSA) or of peroxyadipic acid (NAPAA), N-nonanoylaminoperoxycaproic acid (NAPCA), and mixtures thereof; in one aspect, said preformed peracid comprises phthalimidoperoxyhexanoic acid;

e) said diacyl peroxide may comprise a material selected from the group consisting of dinonanoyl peroxide, didecanoyl peroxide, diundecanoyl peroxide, dilauroyl peroxide, dibenzoyl peroxide, di-(3,5,5-trimethyl hexanoyl) peroxide and mixtures thereof; in one aspect, said diacyl peroxide is, clathrated;

In one aspect of said composition, a) said encapsulate may comprise two or more matrix compositions, said two or more matrix compositions being encapsulated by said encapsulate's shell; and/or b) said composition may comprise two or more different species of said encapsulate.

In one aspect of said composition, said encapsulate may have a stability index of from about 0.8 to about 1, from about 0.9 to about 1, or even from about 0.95 to about 1.

In one aspect of said composition, said encapsulate may have a release index of from about 0.25 to about 1, from about 0.5 to about 1, or even from about 0.85 to about 1.

In one aspect of said composition, said encapsulate may have a matrix composition to shell mass ratio of from about 15:85 to about 95:5, from about 25:75 to about 85:15, or even from about 35:65 to about 75:25.

In one aspect of said composition, said composition may be a consumer product comprising said encapsulate and an adjunct ingredient.

In one aspect of said composition, said composition may comprise a material selected from
  a) an anionic surfactant and/or a nonionic, in one aspect an anionic surfactant
  b) a solvent, in one aspect said solvent may comprise butoxypropoxypropanol and/or glycerol;
  c) water, in one aspect, based on total composition weight, less than about 10% water
  d) an external structuring system, in one aspect, said structuring system may be selected from the group consisting of polysaccharides, di-benzylidene polyol acetal derivative, bacterial cellulose, coated bacterial cellulose, non-polymeric crystalline hydroxyl-functional materials, polymers, amido gellants and mixtures thereof
  e) optionally one or more materials selected from the group consisting of:
    (i) a bleach compatible clay clean polymer, in one aspect said bleach compatible clay clean polymer may be selected from the group consisting of ethoxylated hexamethylene diamine dimethyl quat, ethoxysulfated hexamethylene diamine dimethyl quat and mixtures thereof.
    (ii) a brightener, in one aspect said brightener may comprise a fluorescent brightener selected from disodium 4,4'-bis(2-sulfostyryl)biphenyl and/or bis(sulfobenzofuranyl)biphenyl.
    (iii) a builder, in one aspect said builder may comprise sodium citrate
    (iv) a chelant, in one aspect said chelant may comprise 1-Hydroxy Ethylidene-1,1-Diphosphonic Acid (HEDP)

Process of Making Consumer Products

In one aspect of said process of making a consumer product comprising an encapsulate composition comprising encapsulates, said process may comprise making an encapsulate by spraying a matrix composition and an encapsulating solution in a chamber at a temperature of from about 25° C. to about 150° C. by using a flow focusing nozzle. In one aspect, said flow focusing nozzle comprises a concentric nozzle. In one aspect, said concentric nozzle has an internal diameter from about 100 microns to about 500 microns, or even from about 250 microns to about 400 microns. In one aspect, said concentric nozzle has an external diameter from about 200 microns to about 1,000 microns, from about 350 microns to about 850 microns, or even from about 500 microns to about 750 micro, said matrix composition comprising, based on total solution weight:
  a) from about 0.01% to about 10% of a matrix network material, said matrix network material comprising a self-assembled matrix network material having a molecular weight from about 150 g/mol to about 1500 g/mol, from about 250 g/mol to about 1200 g/mol, or even from about 500 g/mol to about 850 g/mol and said matrix network material having a pKa of from about 3.5 to about 6 or even from about 4.5 to about 5.5.
  b) from about 0.1% to about 35% of a base. In one aspect such base comprises sodium hydroxide, potassium hydroxide, sodium carbonate, ammonia, sodium acetate, monoethanol amine, calcium hydroxide, barium hydroxide, potassium carbonate, magnesium hydroxide and mixtures thereof.
  c) from about 0.2% to about 90% of the matrix benefit agent cores, said benefit agent cores comprising a material selected from the group consisting of a preformed peracid, a metal catalyst, a bleach activator, a bleach booster and a diacyl peroxide.
  d) from about 0.1 to about 35% of a buffer or buffer precursor to said first composition. In one aspect such buffer precursor comprises gluco-δ-lactone.

said encapsulating solution comprising, based on total solution weight, from about 2 to about 20% of a material that is suspended or dissolved in said encapsulating solution, and one or more solvents. In one aspect such solvent may comprise water, ethanol, acetone, dichloromethane and mixtures thereof. In one aspect, such material may comprise
  a) polyvinyl pyrrolidone, in one aspect, such material may comprise polyvinyl pyrrolidone, polyvinyl pyrrolidone styrene copolymers, polyvinyl pyrrolidone vinyl acetate copolymers, polyvinyl pyrrolidone imidazole copolymers and mixtures thereof;
  b) polyvinyl alcohol derivative, in one aspect such material may comprise polyvinyl alcohol, polyvinyl acetate, polyvinyl alcohol 2-acrylamide-2-methylpropane sulfonate copolymers, copolymers of polyvinyl alcohol derived from monomers comprising primary and secondary amine, polyvinyl alcohol imidazoles copolymers and mixtures thereof;
  c) a material comprising a polymer with a cloud point from about 0° C. to about 120° C., or even from about 20° C. to about 60° C., in one aspect, such material may comprise poly-(N-isopropylacrylamide), poly-(vinyl alcohol-co-vinyl acetate), poly-(acrylamide-co-diacetoneacrylamide) or ethyl cellulose.
  e) a material comprising a cellulosic polymer, in one aspect such material may comprise starch, cellulose acetate, cellulose acetate phthalate, hydroxylpropyl methyl cellulose, methyl cellulose, ethyl cellulose, hydroxypropyl methylcellulose phthalate and mixtures thereof, in one aspect such starch may comprise a octenyl succinated starch, a hydroxyethylated starch, a hydroxypropylated starch and mixtures thereof.
  f) a wax, in one aspect such wax having a melting point from about 35° C. to about 75° C.
  g) a non-cellulosic, natural polymer, in one aspect such material may comprise shellac, zein and mixtures thereof;

optionally concentrating the number of encapsulates in said encapsulate composition and mixing with one or more adjunct ingredients In one aspect of said process of making a consumer product comprising an encapsulate composition comprising encapsulates, said process may comprise making an encapsulate by spraying a matrix composition and an encapsulating solution using electrospinning needles. In one aspect, said electrospinning needles may comprise a concentric needle. In one aspect, said concentric needle has an internal diameter from about 100 microns to about 2,000 microns, or even from about 250 microns to about 1,000 microns. In one aspect, said concentric needle has an external diameter from about 200 microns to about 4,000 microns, from about 350 microns to about 1,500 microns, or even from about 500 microns to about 1,000 microns, said matrix composition comprising, based on total solution weight:
  a) from about 0.01% to about 10% of a matrix network material, said matrix network material comprising a self-assembled matrix network material having a molecular weight from about 150 g/mol to about 1500 g/mol, from about 250 g/mol to about 1200 g/mol, or even from about 500 g/mol to about 850 g/mol and said matrix network material having a pKa of from about 3.5 to about 6 or even from about 4.5 to about 5.5.
  b) from about 0.1% to about 35% of a base. In one aspect such base comprises sodium hydroxide, potassium hydroxide, sodium carbonate, ammonia, sodium acetate, monoethanol amine, calcium hydroxide, barium hydroxide, potassium carbonate, magnesium hydroxide and mixtures thereof.
  c) from about 0.2% to about 90% of the matrix benefit agent cores, said benefit agent cores comprising a material selected from the group consisting of a preformed peracid, a metal catalyst, a bleach activator, a bleach booster and a diacyl peroxide.
  d) from about 0.1 to about 35% of a buffer or buffer precursor to said first composition. In one aspect such buffer precursor comprises gluco-δ-lactone.
said encapsulating solution comprising, based on total solution weight, from about 2 to about 20% of a material that is suspended or dissolved in said encapsulating solution, and one or more solvents. In one aspect such solvent may comprise water, ethanol, acetone, dichloromethane and mixtures thereof. In one aspect, such material may comprise
  a) polyvinyl pyrrolidone, in one aspect, such material may comprise polyvinyl pyrrolidone, polyvinyl pyrrolidone styrene copolymers, polyvinyl pyrrolidone vinyl acetate copolymers, polyvinyl pyrrolidone imidazole copolymers and mixtures thereof;
  b) polyvinyl alcohol derivative, in one aspect such material may comprise polyvinyl alcohol, polyvinyl acetate, polyvinyl alcohol 2-acrylamide-2-methylpropane sulfonate copolymers, copolymers of polyvinyl alcohol derived from monomers comprising primary and secondary amine, polyvinyl alcohol imidazoles copolymers and mixtures thereof;
  c) a material comprising a polymer with a cloud point from about 0° C. to about 120° C., or even from about 20° C. to about 60° C., in one aspect, such material may comprise poly-(N-isopropylacrylamide), poly-(vinyl alcohol-co-vinyl acetate), poly-(acrylamide-co-diacetoneacrylamide) or ethyl cellulose.
  e) a material comprising a cellulosic polymer, in one aspect such material may comprise starch, cellulose acetate, cellulose acetate phthalate, hydroxylpropyl methyl cellulose, methyl cellulose, ethyl cellulose, hydroxypropyl methylcellulose phthalate and mixtures thereof, in one aspect such starch may comprise a octenyl succinated starch, a hydroxyethylated starch, a hydroxypropylated starch and mixtures thereof.
  f) a wax, in one aspect such wax having a melting point from about 35° C. to about 75° C.
  g) a non-cellulosic, natural polymer, in one aspect such material may comprise shellac, zein and mixtures thereof;
optionally concentrating the number of encapsulates in said encapsulate composition and mixing with one or more adjunct ingredients In one aspect of said process of making a consumer product comprising an encapsulate composition, said process may comprise forming an emulsion, optionally by employing a micro device, in one aspect said micro-device is selected from the group consisting of a cross flow membrane, and/or a flow focusing technology, said emulsion comprising the following components:

a) a composition comprising a matrix material and a first wall material; and
  b) a hydrophobic liquid, In one aspect, said hydrophobic liquid comprises a hydrophobic solvent, an oil and mixtures thereof. In one aspect, such hydrophobic solvent comprises toluene, heptane, hexane, chloroform, benzene, tetrahydrofuran, dichloromethane, dimethylsulfoxide, and mixtures thereof. In one aspect such oil comprises mineral oil, canola oil, cedar oil, corn oil, jojoba oil, peanut oil, olive oil, safflower oil, sunflower seed oil, sunflower oil, sesame oil, soybean oil, paraffin oil, silicone oil and mixtures thereof, based on total wall material solution weight,
  said emulsion being formed at temperature of from about 0° C. to about 30° C., said emulsion formation comprising combining said components, agitating said components for about 2 minutes to about 15 minutes at a speed from about 600 rpm to about 1500 rpm, adding a second wall material and permitting said components of said emulsion and said second wall material to react while agitating said components of said emulsion and said second wall material at a speed from about 150 rpm to about 500 rpm, at a temperature of from about 0° C. to about 30° C., for a time of from about 15 minutes to about 24 hours,
said composition comprising a matrix material and a first wall material comprising, based on total composition comprising a matrix material and a first wall material weight,
  a. from about 0.01% to about 10% of a matrix network material, said matrix network material comprising a self-assembled matrix network material having a molecular weight from about 150 g/mol to about 1,500 g/mol, from about 250 g/mol to about 1200 g/mol, or even from about 500 g/mol to about 850 g/mol and said matrix network material having a pKa of from about 3.5 to about 6 or even from about 4.5 to about 5.5.
  b) from about 0.1% to about 70% of a base and/or a hydrophilic monomer. In one aspect, such hydrophilic monomer comprising diamines, triamines, diols and mixtures thereof. In one aspect, such diamines and triamines may comprise diethylene triamine, hexamethylene diamine, ethylene diamine and mixtures thereof. In one aspect, such diol may comprise ethylene glycol, 1,2-propanediol, 1,3-propanediol, 1-propen-1,3-diol, 1,4-butanediol, 1,3-butanodiol, 1,2-butanediol, 3-butene-1,2-diol, 3-butene-1,4-diol, 1,5-pentanediol, 1-penten-1,5-diol, 1,6-hexanediol, 3,4-dihydroxy-3-cyclobutene-1,2-dione, 5-hydroxy-2-(hydroxymethyl)-4H-pyran-4-one, (2E)-2,3-dihydroxy-2-butenedioic acid hydrate, 2,3,5,6-tetrahydroxybenzo-1,4-quinone, 4,4-dimethyl-1,2-cyclopentanediol, 3-methyl-1,3,5-pentanetriol, 3-methyl-1,5-pentanediol, (1S,2S)-1,2-cyclopentanediol, 1,3-cyclohexanediol, 1,5-hexanediol, 1,2,6-hexanetriol, 1,2,4-butanetriol and mixtures thereof. In one aspect such base comprises sodium hydroxide, potassium hydroxide, sodium carbonate, ammonia, sodium acetate, monoethylene amine, calcium hydroxide, barium hydroxide, potassium carbonate, magnesium hydroxide and mixtures thereof.
  a. from about 0.2% to about 90% of the matrix benefit agent cores, said benefit agent cores comprising a material selected from the group consisting of a preformed peracid, a metal catalyst, a bleach activator, a bleach booster and a diacyl peroxide.
  c) from about 0.1 to about 35% of a buffer or buffer precursor. In one aspect such buffer precursor comprises gluco-δ-lactone.

said second wall material comprising from about 2 to about 70% of a hydrophobic monomer suspended and/or dissolved in a hydrophobic liquid. In one aspect such hydrophobic monomer comprises di- and/or tri-acyl chlorides, diisocyanates, bischloroformates and mixtures thereof. In one aspect, such di- and/or tri-acyl chlorides comprises trimesoyl chloride, teraphthaloyl chloride, and mixtures thereof. In one aspect, such diisocyanate comprises 1-isocianato-4-[(4-fenilisocianato)metil]benzene, 2,4-diisocyanato-1-methyl-benzene, 1,6-diisocyanatohexane, 5-isocyanato-1-(isocyanatomethyl)-1,3,3-trimethyl-cyclohexane and mixtures thereof. In one aspect, such bischloroformates comprises bisphenol A bis(chloroformate), bisphenol Z bis(chloroformate) and mixtures thereof.

a. optionally, from about 0.2% to about 5% of an emulsifier, said emulsifier having a HLB (hydrophilic-hydrophobic balance/Griffing index) from about 0 to about 8, or even from about 2 to about 7. In one aspect such emulsifier comprises polyethylene-block-poly(ethylene glycol), polyethylene glycol oleyl ether, 2,4,7,9-Tetramethyl-5-decyne-4,7-diol, polyethylene glycol hexadecyl ether, polyoxyethylene (2) nonylphenyl ether, polyoxyethylene (2) isooctylphenyl ether, sorbitan monooleate, sorbitan sesquioleate, and mixtures thereof.

optionally combining any scavenger material, neutralizing agent, structurant, salts and/or anti-agglomeration agent with said third composition during step g.) or thereafter; optionally concentrating the number of encapsulates in said encapsulate composition in one aspect by spray drying or agglomerating said encapsulate composition and combining said encapsulate composition with one or more adjunct ingredients.

Adjunct Ingredients

For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components supplied by the recited particle. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

Each adjunct ingredient is not essential to Applicants' compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. It is understood that such adjuncts may form a product matrix that is combined with the encapsulates disclosed herein to form a finished consumer product. Generally, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Structurants—Non-limiting examples of suitable structurants are:

I. Di-Benzylidene Polyol Acetal Derivative

The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. Non-limiting examples of suitable DBPA molecules are disclosed in U.S. 61/167,604. In one aspect, the DBPA derivative may comprise a dibenzylidene sorbitol acetal derivative (DBS). Said DBS derivative may be selected from the group consisting of: 1,3:2,4-dibenzylidene sorbitol; 1,3:2,4-di(p-methylbenzylidene) sorbitol; 1,3:2,4-di(p-chlorobenzylidene) sorbitol; 1,3:2,4-di(2,4-dimethyldibenzylidene) sorbitol; 1,3:2,4-di(p-ethylbenzylidene) sorbitol; and 1,3:2,4-di(3,4-dimethyldibenzylidene) sorbitol or mixtures thereof. These and other suitable DBS derivatives are disclosed in U.S. Pat. No. 6,102,999, column 2 line 43 to column 3 line 65.

ii. Bacterial Cellulose

The fluid detergent composition may also comprise from about 0.005% to about 1.0% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like. Some examples of suitable bacterial cellulose can be found in U.S. Pat. Nos. 6,967,027; 5,207,826; 4,487,634; 4,373,702; 4,863,565 and US 2007/0027108. In one aspect, said fibres have cross sectional dimensions of 1.6 nm to 3.2 nm by 5.8 nm to 133 nm. Additionally, the bacterial cellulose fibres have an average microfibre length of at least about 100 nm, or from about 100 to about 1,500 nm. In one aspect, the bacterial cellulose microfibres have an aspect ratio, meaning the average microfibre length divided by the widest cross sectional microfibre width, of from about 100:1 to about 400:1, or even from about 200:1 to about 300:1.

iii. Coated Bacterial Cellulose

In one aspect, the bacterial cellulose is at least partially coated with a polymeric thickener. The at least partially coated bacterial cellulose can be prepared in accordance with the methods disclosed in US 2007/0027108 paragraphs 8 to 19. In one aspect the at least partially coated bacterial cellulose comprises from about 0.1% to about 5%, or even from about 0.5% to about 3.0%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

iv. Non-Polymeric Crystalline Hydroxyl-Functional Materials

In one aspect, the composition may further comprise from about 0.01 to about 1% by weight of the composition of a non-polymeric crystalline, hydroxyl functional structurant. Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

v. Polymeric Structuring Agents

Fluid detergent compositions of the present invention may comprise from about 0.01 to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon inc under the tradename Carbopol Aqua 30.

vi. Di-Amido-Gellants

In one aspect, the external structuring system may comprise a di-amido gellant having a molecular weight from 150 g/mol to 1,500 g/mol, or between 500 g/mol and 900 g/mol. Such di-amido gellants may comprise at least two nitrogen atoms, wherein at least two of said nitrogen atoms form amido functional substitution groups. In one aspect, the amido groups are different. In another aspect, the amido functional groups are the same. The di-amido gellant has the following formula:

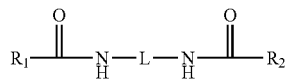

wherein:

$R_1$ and $R_2$ is an amino functional end-group, or even amido functional end-group, in one aspect $R_1$ and $R_2$ may comprise a pH-tuneable group, wherein the pH tuneable amido-gellant may have a pKa of from about 1 to about 30, or even from about 2 to about 10. In one aspect, the pH tuneable group may comprise a pyridine. In one aspect, $R_1$ and $R_2$ may be different. In another aspect, may be the same.

L is a linking moeity of molecular weight from 14 to 500 g/mol. In one aspect, L may comprise a carbon chain comprising between 2 and 20 carbon atoms. In another aspect, L may comprise a pH-tuneable group. In one aspect, the pH tuneable group is a secondary amine.

In one aspect, at least one of $R_1$, $R_2$ or L may comprise a pH-tuneable group.

Non-limiting examples of di-amido gellants are:

N,N'-(2S,2'S)-1,1'-(dodecane-1,12-diylbis(azanediyl))bis(3-methyl-1-oxobutane-2,1-diyl)diisonicotinamide

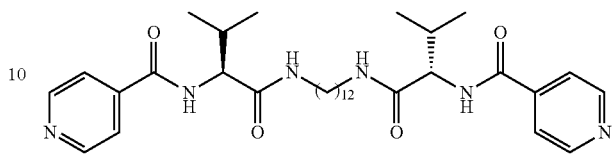

dibenzyl (2S,2'S)-1,1'-(propane-1,3-diylbis(azanediyl))bis(3-methyl-1-oxobutane-2,1-diyl)dicarbamate

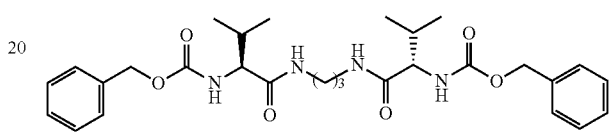

dibenzyl (2S,2'S)-1,1'-(dodecane-1,12-diylbis(azanediyl))bis(1-oxo-3-phenylpropane-2,1-diyl)dicarbamate

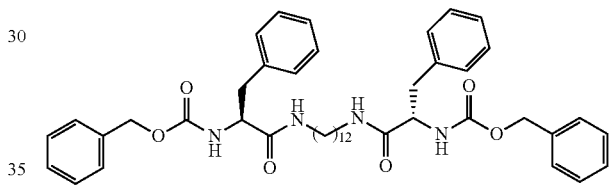

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Method of Use

Certain of the consumer products disclosed herein can be used to clean or treat a situs inter alia a surface or fabric. Typically at least a portion of the situs is contacted with an embodiment of Applicants' consumer product, in neat form or diluted in a liquor, for example, a wash liquor and then the situs may be optionally washed and/or rinsed. In one aspect, a situs is optionally washed and/or rinsed, contacted with an aspect of the consumer product and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

The employing one or more of the aforementioned methods result in a treated situs.

TEST METHODS

It is understood that the test methods that are disclosed in the Test Methods Section of the present application should be used to determine the respective values of the parameters of Applicants' invention as such invention is described and claimed herein.

(1) Mean Particle Size for Slurries/Liquids Containing Particles in the Range of 1 to 500 Microns The mean particle size of the particles is determined using a Lasentec M500L-316-K supplied by Mettler-Toledo, Inc., 1900 Polaris Parkway, Columbus, Ohio, 43240, US. The equipment is setup (Lasentec, FBRM Control Interface, version 6.0) as described in the Lasentec manual, issued February 2000. Software setup and sample analysis is performed using Windows software (Windows XP, version 2002) in the WINDOWS manual. When the particles are collected as solid particles they are uniformly dispersed in deionized water so the test can be performed.

(2) Benefit Agent Release Test

Materials and Instruments Needed:
1. launder-o-meter (launder-o-meter procedures are described in the Technical Manual of the AATCC)
2. Test pieces of soiled fabric 10×10 cm as described in JAOCS, Vol. 66, n.1 (January 1989)
3. A canister of 50 steel balls of 6 mm diameter
4. Industrial water (2.5 mmol/L hardness)
5. Detergent composition containing particles having a core comprising a benefit agent.

Procedure:
Prepare a stainless-steel launder-o-meter container and add 250 mL of water at 30° C., 2.5 g of a liquid detergent composition containing particles containing a benefit agent, three test pieces of soiled fabric 10×10 cm and 50 steel balls. Containers are place in the launder-ometer and they are rotated for 40 minutes at 42 rpm. Every 5 minutes a sample is taken for analytical measurement of the benefit agent. The analysis is performed in accordance with the applicable protocol that is listed below:

A. Analytical test for preformed peracids and bleach activators: Hydrogen peroxide in liquid bleaches liberates iodine from an acidified potassium iodide solution. The free iodine is titrated potentiometrically with a standardized thiosulphate solution $$\text{Bleach component} + 2I^- + 2H^+ \rightarrow I_2 + 2\,H_2O \quad [1]$$

$$I_2 + I^- \leftrightarrow I_3^- \quad [2]$$

$$I_3^- + 2S_2O_3^{2-} \rightarrow 3I^- + S_4O_6 \quad [3]$$

The bleach component can be a preformed peracid or a peracid generated by a bleach activator. The method measures the total amount of bleach. In case the bleach is generated from a bleach activator reacting with hydrogen peroxide, Catalase needs to be added after the peracid generation. Catalase destroys hydrogen peroxide without influencing the peracid and only the peracid is present for further analysis.

Equipment:
Autotitrator (fe Metrohm 809) connected to a computer
Redox electrode (fe Metrohm 6.0431.100)

Chemicals:
Glacial Acetic Acid (VWR 1.00063)
KI 3 M (Sigma Aldrich 35175)
$Na_2S_2O_3$ 0.01 N (38243, Sigma Aldrich)
Catalase from bovine lever Fluka Biochemica 60640±260000 U/mL
Sodium percarbonate 10% aqueous solution. In order to prepare this solution, add 100 grams sodium carbonate (VWR ALFAA16045) to 900 mL deionized water under continuous stirring.

Procedure:
1. Preformed Peracids in Absence of Additional Hydrogen Peroxide:
   a. weigh×grams of sample in order to have between 0.05 and 1 grams of preformed peracid.
   b. Add 50 mL water
   c. Add 10 mL of acetic acid.
   d. Stir for 1 minute
   e. Add 4 mL of KI solution
   f. Titrate with $Na_2S_2O_3$ with the redox electrode until the first equivalent point
   g. Calculate the release index of peroxide/peracid:

$$\text{Release index} = \frac{V \cdot N \cdot M_w}{G \cdot 2000}$$

wherein V is the measured volume in mL, N is the normality of the sodium thiosulfate solution, Mw the molecular weight of the preformed peracid and G the grams, based on 100% purity, of the preformed peracid weight for the titration.

2. In Situ Formed Peracids (In Situ Reaction of Hydrogen Peroxide and a Bleach Activator)
   a. Weigh×grams of sample in order to have between 0.05 and 1 grams of bleach activator.
   b. Add 50 mL of percarbonate solution
   c. Stir for 10 minutes (to enable peracid formation)
   d. Add 0.5 mL of Catalase
   e. Stir for at least 1 minute (maximum 5 minutes)
   f. Add 10 mL of acetic acid
   g. Add 4 mL KI solution
   h. Titrate with $Na_2S_2O_3$ with the redox electrode until the first equivalent point
   i. Calculate the release index of peracid:

$$\text{Release index} = \frac{V \cdot N \cdot M_w}{G \cdot 2000}$$

wherein V is the measured volume in mL, N is the normality of the sodium thiosulfate solution, Mw the molecular weight of the bleach activator and G the grams, based on 100% purity, of the bleach activator weight for the titration.

B. Analytical Test for Metal Catalysts: Photometric Method

The activity of the bleach catalyst is measured by means of a colorimetric reaction with a specific dye.
   a. Preparation of a calibration curve: Add 40 µL of a 10,000 ppm detergent solution like the ones described in examples 4, 5 and 6, without particles containing X ppm of the metal catalyst in deionized water to 150 µL of Chicago sky blue reagent and incubate at 37° C. for 3 minutes (see table below). After incubation an absorbance measure of the solution of detergent and dye is made at 600 nm (Abs 1). Add 60 µL of the hydrogen peroxide reagent to the solution and incubate at 37° C. for 30 minutes. Measure the absorbance of this solution at 600 nm after incubation (Abs 2). Repeat this with different levels of metal catalyst according to following table:

TABLE 2

Data for calibration curve

| Sample | X ppm metal catalyst | Abs 1 | Abs 2 | ABS = Abs 1 − Abs 2 |
|---|---|---|---|---|
| 0 | 0 | | | |
| 1 | 0.05 | | | |
| 2 | 0.10 | | | |
| 3 | 0.20 | | | |
| 4 | 0.30 | | | |
| 5 | 0.40 | | | |
| 6 | 0.50 | | | |
| 7 | 0.60 | | | |
| 8 | 0.80 | | | |
| 9 | 1.00 | | | |
| 10 | 1.25 | | | |
| 11 | 1.50 | | | |
| 12 | 1.75 | | | |
| 13 | 2.00 | | | |
| 14 | 2.50 | | | |
| 15 | 3.00 | | | |

Subtract the initial measured absorbance (Abs 1) from the final (Abs 2) and plot a calibration curve (polynomial fit).
   b. Measure 40 µL of the sampled wash solution and determine the concentration of metal catalyst in the wash by using the calibration curve.
   c. Determine the release index:

$$\text{Release index} = \frac{C_{wash}}{C_{total}}$$

wherein $C_{wash}$ is the concentration determined in the wash in ppm and $C_{total}$ is the total amount of metal catalyst in the wash in ppm (total encapsulated).

C. Analytical test for bleach boosters: Isoquinolinium class materials and the activated intermediate can be measured by mass spectrometry. Depending upon the response of the individual molecule, electrospray mass spectrometry operated in positive or negative ion is used to measure the isoquinolinium and the oxidized intermediate. MS analysis is done either by direct infusion or by injecting discrete amounts of diluted sample (flow injection analysis). No HPLC separation is needed.
  a. Eluents: acetonitrile:water (1/1)+1 mmol ammonium acetate.
  b. Instrument settings are optimized for individual molecules to obtain maximum response.
  c. Subsequent measurements are done either in selective ion mode or multiple reaction monitoring.
  d. Samples are diluted in acetonitrile/water 1/1+1 mmol ammonium acetate. Dilution factor depends upon concentration of the isoquinolinium.
  e. MS setup: electrospray in either positive or negative ion mode. When full scan acquisition is desired, both scan modes are alternated.
Release index is calculated using the same formula as described above for metal catalysts.
D. Analytical test for diacyl peroxides: Diacyl peroxides are measured by means of HPLC separation followed by electrochemical detection. A short chain RP column is used for the separation, 5 μm, 250 mm*4.6 mm A typical eluent is water/acetonitrile (250 mL/850 mL) with 0.0025 M ammonium dihydrogen phosphate. The flow rate is set up to 1.0 mL/min and the detection is done by DC amperometry or colorimetry. Samples are diluted in a mixture of acetonitrile and acetic acid glacial in a ratio of 90% acetonitrile and 10% acetic acid glacial prior to analysis. Release index is calculated using the same formula as described above for metal catalysts (3) Stability Index Determination of Benefit Agent on Storage The amount of benefit agent left upon storage of particles containing these benefit agents in a laundry detergent composition, can be determined filtering the particles from the liquid detergent composition, breaking said particles to release the benefit agent and analyzing the amount left of benefit agent upon storage by using standard analytical methods as described below.

Conditions stability test: samples containing 1% of benefit agent in particle form are stored 7 days at 30° C. in a laundry detergent composition.

Filtration: After 7 days at 30° C. samples are filtered using an 8 microns filter (Whatman Int. LTD, supplied by VWR). Particles are rinsed twice with 3 mL of water.

Particles breakage for benefit agent release: Filter paper containing the particles is introduced in a 250 mL glass pot and 100 mL of deionized water is added. A metal ball of 4 cm diameter (Imes, Belgium) is introduced in the glass pot and the glass pot is closed. The mixture containing the particles is kept at 45° C. for 1 hour in a thermo shaker at 135 rpm (Thermo shaker THO 5, Gerhardt) for complete benefit agent release.

Stability index determination: Benefit agent is analyzed according analytical methods described below.
  A. Analytical test for preformed peracids and bleach activators: Hydrogen peroxide in liquid bleaches liberates iodine from an acidified potassium iodide solution. The free iodine is titrated potentiometrically with a standardized thiosulphate solution $$\text{Bleach component} + 2I^- + 2H^+ \rightarrow I_2 + 2H_2O \quad [1]$$

$$I_2 + I^- \leftrightarrow I_3^- \quad [2]$$

$$I_3^- + 2S_2O_3^{2-} \rightarrow 3I^- + S_4O_6 \quad [3]$$

The bleach component can be a preformed peracid or a peracid generated by a bleach activator. The method measures the total amount of bleach. In case the peracid is generated from a bleach activator reacting with hydrogen peroxide, Catalase needs to be added after the peracid generation. Catalase destroys hydrogen peroxide without influencing the peracid and only the peracid is present for further analysis.

Equipment:
Autotitrator (fe Metrohm 809) connected to a PC
Redox electrode (fe Metrohm 6.0431.100)
Chemicals:
Glacial Acetic Acid (VWR 1.00063)
KI 3 M (Sigma Aldrich 35175)
$Na_2S_2O_3$ 0.1 N (VWR 1.09147)
Catalase from bovine lever Fluka Biochemica 60640±260000 U/mL
Sodium percarbonate 10% aqueous solution. In order to prepare this solution, add 100 grams sodium carbonate (VWR ALFAA16045) to 900 mL deionized water under continuous stiffing.

Procedure:
3. Preformed Peracids in Absence of Additional Hydrogen Peroxide:
  a. weigh×grams of sample (broken aged particles) in order to have between 0.5 and 1 grams of preformed peracid.
  b. Add 50 mL water
  c. Add 10 mL of acetic acid.
  d. Stir for 1 minute
  e. Add 4 mL of KI solution
  f. Titrate with $Na_2S_2O_3$ with the redox electrode until the first equivalent point
  g. Calculate the stability index of peroxide/peracid:

$$\text{stability index} = \frac{V \cdot N \cdot M_w}{G \cdot 2000}$$

wherein V is the measured volume in mL, N is the normality of the sodium thiosulfate solution, Mw the molecular weight of the preformed peracid and G the grams, based on 100% purity, of the preformed peracid weight for the titration.

4. In Situ Formed Peracids (In Situ Reaction of Hydrogen Peroxide and a Bleach Activator)
  a. Weigh×grams of sample (broken aged particles) in order to have between 0.5 and 1 grams of bleach activator.
  b. Add 50 mL of percarbonate solution
  c. Stir for 10 minutes (to enable peracid formation)
  d. Add 0.5 mL of Catalase
  e. Stir for at least 1 minute (maximum 5 minutes)
  f. Add 10 mL of acetic acid
  g. Add 4 mL KI solution
  h. Titrate with $Na_2S_2O_3$ with the redox electrode until the first equivalent point
  i. Calculate the stability index of peracid:

$$\text{Stability index} = \frac{V \cdot N \cdot M_w}{G \cdot 2000}$$

wherein V is the measured volume in mL, N is the normality of the sodium thiosulfate solution, Mw the molecular weight of the bleach activator and G the grams, based on 100% purity, of the bleach activator weight for the titration.

B. Analytical Test for Metal Catalysts: Photometric Method

The activity of the bleach catalyst is measured by means of a colorimetric reaction with a specific dye.

a. Preparation of a calibration curve: Add 40 µL of a 10.000 ppm detergent solution like the ones described in examples 4, 5 and 6, without particles containing X ppm of the metal catalyst in deionized water to 150 µL of Chicago sky blue reagent and incubate at 37° C. for 3 minutes (see table below). After incubation an absorbance measure of the solution of detergent and dye is made at 600 nm (Abs 1). Add 60 µL of the hydrogen peroxide reagent to the solution and incubate at 37° C. for 30 minutes. Measure the absorbance of this solution at 600 nm after incubation (Abs 2). Repeat this with different levels of metal catalyst according to following table:

TABLE 3

Data for calibration curve

| Sample | X ppm metal catalyst | Abs 1 | Abs 2 | ABS = Abs 1 − Abs 2 |
|---|---|---|---|---|
| 0 | 0 | | | |
| 1 | 0.05 | | | |
| 2 | 0.10 | | | |
| 3 | 0.20 | | | |
| 4 | 0.30 | | | |
| 5 | 0.40 | | | |
| 6 | 0.50 | | | |
| 7 | 0.60 | | | |
| 8 | 0.80 | | | |
| 9 | 1.00 | | | |
| 10 | 1.25 | | | |
| 11 | 1.50 | | | |
| 12 | 1.75 | | | |
| 13 | 2.00 | | | |
| 14 | 2.50 | | | |
| 15 | 3.00 | | | |

Subtract the initial measured absorbance (Abs 1) from the final (Abs 2) and plot a calibration curve (polynomial fit).

b. Measure 40 µL of the broken aged particles and determine the concentration of metal catalyst in the wash by using the calibration curve.

c. Determine the stability index:

$$\text{Stability index} = \frac{C_{aged\ particles}}{C_{total}}$$

wherein $C_{aged\ particles}$ is the concentration of metal catalyst determined inside the particles after storage in the liquid detergent composition in ppm and $C_{total}$ is the total amount of metal catalyst in the liquid detergent composition in ppm (total encapsulated).

C. Analytical test for bleach boosters: Isoquinolinium class materials and the activated intermediate can be measured by mass spectrometry. Depending upon the response of the individual molecule, electrospray mass spectrometry operated in positive or negative ion is used to measure the isoquinolinium and the oxidized intermediate. MS analysis is done either by direct infusion or by injecting discrete amounts of diluted sample (flow injection analysis). No HPLC separation is needed.

f. Eluens: acetonitrile: water (1/1)+1 mmol ammonium acetate.

g. Instrument settings are optimized for individual molecules to obtain maximum response.

h. Subsequent measurements are done either in selective ion mode or multiple reaction monitoring.

i. Samples are diluted in acetonitrile/water 1/1+1 mmol ammonium acetate. Dilution factor depends upon concentration of the isoquinolinium.

j. MS setup: electrospray in either positive or negative ion mode. When full scan acquisition is desired, both scan modes alternated.

Stability index is calculated using the same formula as described above for metal catalysts.

D. Analytical test for diacyl peroxides: Diacyl peroxides are measured by means of HPLC separation followed by electrochemical detection. A short chain RP column is used for the separation, 5 µm, 250 mm*4.6 mm A typical eluent is water/acetonitrile (250 mL/850 mL) with 0.0025M ammonium dihydrogen phosphate. The flow rate is set up to 1.0 mL/min and the detection is done by DC amperometry or colorimetry. Samples are diluted in a mixture of acetonitrile and acetic acid glacial in a ratio of 90% acetonitrile and 10% acetic acid glacial prior to analysis. Stability index is calculated using the same formula as described above for metal catalysts (4) pH Measurement of a Liquid Detergent Composition pH measurement of a liquid detergent composition may be measured using test method EN 1262.

(5) Minimum Gelling Concentration (MGC)

MGC is calculated by a tube inversion method based on R. G. Weiss, P. Terech; "Molecular Gels: Materials with self-assembled fibrillar structures" 2006 springer, p 243. In order to determine the MGC, three screenings are done:

a) First screening: prepare several vials increasing the pH tuneable amido gellant concentration from 0.5% to 5.0 weight % in 0.5% steps, at the target pH.

b) Determine in which interval the gel is formed (one inverted sample still flowing and the next one is already a strong gel). In case no gel is formed at 5%, higher concentrations are used.

c) Second screening: prepare several vials increasing the pH tuneable amido gellant concentration in 0.1 weight % steps in the interval determined in the first screening, at the target pH.

d) Determine in which interval the gel is formed (one inverted sample still flowing and the next one is already a strong gel)

e) Third screening: in order to have a very precise percentage of the MGC, run a third screening in 0.025 weight % steps in the interval determined in the second screening, at the target pH.

f) The Minimum Gelling Concentration (MGC) is the lowest concentration which forms a gel in the third screening (does not flow on inversion of the sample).

For each screening, samples are prepared and treated as follows: 8 mL vials (Borosilacate glass with Teflon cap, ref. B7857D, Fisher Scientific Bioblock) are filled with 2.0000±0.0005 g (KERN ALJ 120-4 analytical balance with±0.1 mg precision) of water at the target pH for which we want to determine the MGC. The vial is sealed with the screw cap and left for 10 minutes in an ultrasound bath (Elma Transsonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Production of Spray Dried Particles

Matrix composition: Preparing a first composition by adding 1.25 grams of (6S,19S)-6,19-diisopropyl-4,7,18,21-tetraoxo-5,8,17,20-tetraazatetracosane-1,24-dioic acid to 0.5 mL of a 50% sodium hydroxide solution (Reference 415413, Sigma-Aldrich). Then, a second solution is prepared by dissolving 1.83 grams of manganese complex, such as of meso-5,5,7,12,12,14-hexamethyl-1,4,8,11-tetraazacyclotetradecane and racemic-5,5,7,12,12,14-hexamethyl-1,4,8,11-tetraazacyclotetradecane ligands, in 43.92 grams of demineralized water. This second solution is added to the first composition, heated till 45° C. and mixing till complete dissolution of the (6S,19S)-6,19-diisopropyl-4,7,18,21-tetraoxo-5,8,17,20-tetraazatetracosane-1,24-dioic acid. Then, 2.5 grams D-(+)-Gluconic acid δ-lactone (Reference G4750, Sigma Aldrich) are added, mixed till complete dissolution and immediately sprayed, since the gelling occurs in about 30 minutes.
Shell composition: a 2.5% aqueous solution of 30:70 methyl cellulose:polyvinyl alcohol is prepared as follow: 0.75 grams methyl cellulose (Reference M7140, Sigma-Aldrich) and 1.75 grams polyvinyl alcohol (Reference 360627, Sigma-Aldrich) are dissolved in 97.5 grams of demineralized water.
Spray-drying with a concentric flow focusing nozzle with internal diameter of 500 μm and external diameter of 800 μm: the matrix composition is sprayed through the inner nozzle at a flow rate of 10 mL/hour and the shell composition is sprayed through the outer nozzle at a flow rate of 40 mL/hour to achieve core-shell capsules. Particles are dried at 150° C. and with an air flow rate of 0.3 m³/minute.

Example 2

Production of Spray Dried Particles

Matrix composition: Preparing a first composition by adding 1.25 grams of (6S,19S)-6,19-diisopropyl-4,7,18,21-tetraoxo-5,8,17,20-tetraazatetracosane-1,24-dioic acid to 0.5 mL of a 50% sodium hydroxide solution (Reference 415413, Sigma-Aldrich). Then, 43.92 grams of a 0.1% xanthan gum aqueous solution (0.1 grams xanthan gum Kelzan ASX-T from CP Kelco are added to 99.9 grams of demineralized water and mixed till compelte dissolution) are added, the composition is heated till 45° C. and mixed till complete dissolution of the (6S,19S)-6,19-diisopropyl-4,7,18,21-tetraoxo-5,8,17,20-tetraazatetracosane-1,24-dioic acid. Then, 1.83 grams of a micronized N,N,N',N'-Tetraacetylethylenediamine—TAED—(Reference L04353, Alfa Aesar, micronized such that 99% of the particles have a particle size below 5 microns) are dispersed into the first composition. Finally, 2.5 grams D-(+)-Gluconic acid δ-lactone (Reference G4750, Sigma Aldrich) are added, mixed till complete dissolution and immediately sprayed, since the gelling occurs in about 30 minutes.
Shell composition: a 2.5% aqueous solution of 30:70 methyl cellulose:polyvinyl alcohol is prepared as follow: 0.75 grams methyl cellulose (Reference M7140, Sigma-Aldrich) and 1.75 grams polyvinyl alcohol (Reference 360627, Sigma-Aldrich) are dissolved in 97.5 grams of demineralized water.
Spray-drying with a concentric flow focusing nozzle with internal diameter of 500 μm and external diameter of 800 μm: the matrix composition is sprayed through the inner nozzle at a flow rate of 5.6 mL/hour and the shell composition is sprayed through the outer nozzle at a flow rate of 24.4 mL/hour to achieve core-shell capsules. Particles are dried at 100° C. and with an air flow rate of 0.3 m³/minute.
Non-limiting examples of product formulations comprising an encapsulate are summarized in the following table Examples 3, 4 and 5

Liquid Unit Dose

The following are examples of unit dose executions wherein the liquid composition is enclosed within a PVA film. The film used in the present examples is Monosol M8630 76 μm thickness.

|  | 3 | | | 4 | | 5 | | |
|---|---|---|---|---|---|---|---|---|
|  | 3 compartments | | | 2 compartments | | 3 compartments | | |
| Compartment # | A | B | C | D | E | F | G | H |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 10.0 | 20.0 | 25 | 30 |
| Alkyl sulfate |  |  |  | 2.0 |  |  |  |  |
| $C_{12-14}$ alkyl 7-ethoxylate | 17.0 | 17.0 | 17.0 |  | 7.0 | 17.0 | 15 | 10 |

|  | 3<br>3 compartments | | | 4<br>2 compartments | | 5<br>3 compartments | | |
|---|---|---|---|---|---|---|---|---|
| Compartment # | A | B | C | D | E | F | G | H |
| Dosage (g) | 34.0 | 3.5 | 3.5 | 30.0 | 5.0 | 25.0 | 1.5 | 4.0 |
| Ingredients | | | | Weight % | | | | |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | | 10.0 | | | |
| $C_{12-18}$ Fatty acid | 13.0 | 13.0 | 13.0 | | 8.0 | 18.0 | 10 | 15 |
| Sodium citrate | | | | 4.5 | | | | |
| enzymes | 0-3 | 0-3 | 0-3 | 0-3 | | 0-3 | 0-3 | 0-3 |
| Sodium Percarbonate | | | | 11.0 | | | | |
| TAED particles from example 2 | | | | | 50 | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | | 0.4 | |
| Brightener | 0.2 | 0.2 | 0.2 | 0.3 | | | 0.3 | |
| Perfume microcapsules | 0.4 | | | | 5.0 | | | |
| Particles from example 1 | 0.5 | | | | | | | 2.0 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine)[2] | To pH 8.0 for liquids<br>To RA >5.0 for powders | | | | | | | |
| Solvents (1,2 propanediol, ethanol), Sulfate | To 100p | | | | | | | |

[1] Polyethylenimine (MW = 600) with 20 ethoxylate groups per —NH.
[2] RA = Reserve Alkalinity (g NaOH/dose)

|  | Example 3 | Example 4 | Example 5 |
|---|---|---|---|
| Amount of fluid composition in the unit dose article | 40 mL | 35 mL | 31 mL |
| Ingredients | | Weight % | |
| $C_{11-16}$ Alkylbenzene sulfonic acid | 18.0 | 12.5 | 19.0 |
| $C_{12-14}$ Alkyl sulfate | — | 2.0 | — |
| $C_{12-14}$ Alkyl 7-ethoxylate | 17.0 | 17.0 | 16.0 |
| $C_{12-14}$ Alkyl ethoxy 3 sulfate | 7.5 | — | 7.0 |
| Citric acid | 3.5 | 1.0 | 2.0 |
| Chloryhidric acid | — | 0.8 | 0.3 |
| $C_{12-18}$ Fatty acid | 10.0 | 17.0 | 15.0 |
| Sodium citrate | — | 4.0 | — |
| enzymes | 0-3.0 | 0-3.0 | 0-3.0 |
| Ethoxylated Polyethylenimine[1] | 2.2 | — | — |
| Hydroxyethane diphosphonic acid | 0.6 | 0.5 | 2.2 |
| Amphiphilic alkoxylated grease cleaning polymer[2] | 2.5 | — | 3.5 |
| Ethylene diamine tetra(methylene phosphonic) acid | — | — | 0.4 |
| Brightener | 0.2 | 0.3 | 0.3 |
| Perfume microcapsules[4] | 0.4 | — | — |
| Water | 20.5 | 22.5 | 15.5 |
| Calcium chloride | — | — | 0.01 |
| Perfume | 1.7 | 0.6 | 1.6 |
| N,N'-(2S,2'S)-1,1'-(dodecane-1,12-diylbis(azanediyl))bis(3-methyl-l-oxobutane-2,1-diyl)diisonicotinamide | 0.30 | 0.28 | — |
| N-[(1S)-2-methyl-1-[8-[[(2S)-3-methyl-2-(pyridine-4-carbonylamino)pentanoyl]amino]octylcarbamoyl]butyl]pyridine-4-carboxamide | — | — | 0.35 |

-continued

|  | Example 3 | Example 4 | Example 5 |
|---|---|---|---|
| Minors (antioxidant, sulfite, aesthetics, . . . ) | 2.0 | 4.0 | 2.3 |
| Buffers (monoethanolamine) |  | To pH 8.0 |  |
| Solvents (1,2 propanediol, ethanol) |  | To 100 parts |  |

[1]Polyethylenimine (MW = 600) with 20 ethoxylate groups per —NH.
[2]PG617 or PG640 (BASF, Germany)
3 coated particles as described in example 2.
[4]Perfume microcapsules can be prepared as follows: 25 grams of butyl acrylate-acrylic acid copolymer emulsifier (Colloid C351, 25% solids, pka 4.5-4.7, (Kemira Chemicals, Inc. Kennesaw, Georgia U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson , New Jersey, U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5- 4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Missouri, U.S.A.) is added to the suspension.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition having a pH of from about 6.5 to about 14, said composition comprising an encapsulate having a diameter of from about 10 microns to about 450 microns, said encapsulate comprising a shell and a matrix composition, said shell encapsulating said matrix composition, said matrix composition having a pH from about 3.5 to about 6, said matrix composition comprising a matrix network material and matrix benefit agent cores, said matrix benefit agent cores being entrapped in said matrix network material,
wherein said matrix composition comprises, based on total matrix composition weight, from 0.01 wt % to 10 wt % of a matrix network material having a formula:

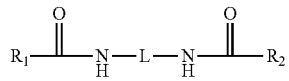

wherein $R_1$ and $R_2$ are aminofunctional end-groups; L is a backbone moiety having molecular weight from 14 to 500 g/mol; and at least one of L, $R_1$ or $R_2$ comprises a pH-sensitive group.

2. The composition of claim 1, wherein said matrix composition comprises a self-assembled matrix network material having a molecular weight from about 150 g/mol to about 1,500 g/mol.

3. The composition of claim 1, said matrix network material is in its neutral viscosity building form at a pH of from about 3.5 to about 6.

4. The composition of claim 1, said matrix network material having a pKa of from about 1 to about 14.

5. The matrix network material from claim 1, wherein $R_1$ and $R_2$ are amidofunctional end-groups.

6. The composition of claim 1, wherein said matrix network material has a minimum gelling concentration (MGC) of from 0.1 to 100 mg/mL.

7. The composition of claim 1, wherein said matrix composition comprises a buffer and/or buffer precursor.

8. The composition of claim 1, wherein said matrix composition comprises a polysaccharide.

9. The composition of claim 1, wherein said shell comprises a material selected from the group consisting of
a) a material comprising polyvinyl pyrrolidone;
b) polymers derived from hydrophilic monomers comprising diamines, triamines, diols and mixtures thereof;
c) polymers derived from hydrophobic monomers comprising di- and or tri-acyl chlorides, diisocyanates, bischloroformates and mixtures thereof;
d) a material comprising a polyvinyl alcohol derivative;
e) a material comprising a polymer with a cloud point from about 0° to about 120° C., or even from about 20° to about 60° C.;
f) a material comprising a cellulosic polymer;
g) a material comprising a wax, such wax having a melting point from about 35° C. to about 75° C.;
h) a material comprising a non-cellulosic, natural polymer;
and said matrix benefit agent cores comprise a material selected from the group consisting of a preformed peracid, a metal catalyst, a bleach activator, a bleach booster and a diacyl peroxide.

10. The composition of claim 9, wherein:
a) said metal catalyst comprises a material selected from the group consisting of dichloro-1,4-diethyl-1,4,8,11-tetraaazabicyclo[6.6.2]hexadecane manganese(II); dichloro-1,4-dimethyl-1,4,8,11-tetraaazabicyclo[6.6.2] hexadecane manganese(II) and mixtures thereof;
b) said bleach booster comprises material selected from the group consisting of 2-[3-[(2-hexyldodecyl)oxy]-2-(sulfooxy)propyl]-3,4-dihydroisoquinolinium, inner salt; 3,4-dihydro-2-[3-[(2-pentylundecyl)oxy]-2-(sulfooxy)propyl]isoquinolinium, inner salt; 2-[3-[(2-butyldecyl)oxy]-2-(sulfooxy)propyl]-3,4-dihydroisoquinolinium, inner salt; 3,4-dihydro-2-[3-(octadecyloxy)-2-(sulfooxy)propyl]isoquinolinium, inner salt; 2-[3-(hexadecyloxy)-2-(sulfooxy)propyl]-3,4-dihydroisoquinolinium, inner salt; 3,4-dihydro-2-[2-(sulfooxy)-3-(tetradecyloxy)propyl]isoquinolinium, inner salt; 2-[3-(dodecyloxy)-2-(sulfooxy)propyl]-3,4-dihydroisoquinolinium, inner salt; 2-[3-[(3-hexyldecyl)oxy]-2-(sulfooxy)propyl]-3,4-dihydroisoquinolinium, inner salt; 3,4-dihydro-2-[3-[(2-pentylnonyl)oxy]-2-(sulfooxy)propyl]isoquinolinium, inner salt; 3,4-dihydro-2-[3-[(2-propylheptyl)oxy]-2-(sulfooxy)propyl]isoquinolinium, inner salt; 2-[3-[(2-butyloctyl)oxy]-2-(sulfooxy)propyl]-3,4-dihydroisoquinolinium, inner salt; 2-[3-(decyloxy)-2-(sulfooxy)propyl]-3,4-dihydroisoquinolinium, inner salt; 3,4-dihydro-2-[3-(octyloxy)-2-(sulfooxy)propyl]isoquinolinium, inner salt; 2-[3-[(2-ethylhexyl)oxy]-2-(sulfooxy)propyl]-3,4-dihydroisoquinolinium, inner salt and mixtures thereof;
c) said bleach activator comprises a material selected from the group consisting of tetraacetyl ethylene diamine (TAED); benzoylcaprolactam (BzCL); 4-nitrobenzoylcaprolactam; 3-chlorobenzoyl¬caprolactam; benzoyloxybenzenesulphonate (BOBS); nonanoyloxybenzene¬sulphonate (NOBS); phenyl benzoate (PhBz); decanoyloxybenzoic acid (DOBA); (6-octanamidocaproyl)oxybenzenesulfonate; (6-nonanamidocaproyl) oxybenzenesulfonate; (6-decanamidocaproyl)oxybenzenesulfonate and mixtures thereof;
d) said preformed peracid comprises a material selected from the group consisting of peroxymonosulfuric acids; perimidic acids; percabonic acids; percarboxilic acids and salts of said acids; in one aspect said percarboxilic acids and salts thereof may be phthalimidoperoxyhexanoic acid, 1,12-diperoxydodecanedioic acid; or monoperoxyphthalic acid (magnesium salt hexahydrate); amidoperoxyacids, in one aspect, said amidoperoxyacids may be N,N'-terephthaloyl-di(6-aminocaproic acid), a mononmonoylamide of either peroxysuccinic acid (NAPSA) or of peroxyadipic acid (NAPAA), N-nonanoylaminoperoxycaproic acid (NAPCA), and mixtures thereof; in one aspect, said preformed peracid comprises phthalimidoperoxyhexanoic acid;
e) said diacyl peroxide comprises a material selected from the group consisting of dinonanoyl peroxide, didecanoyl peroxide, diundecanoyl peroxide, dilauroyl peroxide, dibenzoyl peroxide, di-(3,5,5-trimethyl hexanoyl) peroxide and mixtures thereof; in one aspect, said diacyl peroxide is, clathrated.

11. The composition of claim 1, wherein:
a) said encapsulate comprises two or more matrix compositions, said two or more matrix compositions being encapsulated by said encapsulate's shell; and/or
b) said composition comprises two or more different species of said encapsulate.

12. The composition of claim 1, wherein said encapsulate has a stability index of from about 0.8 to about 1.

13. The composition of claim 1, wherein said encapsulate has a release index of from about 0.25 to about 1.

14. The composition of claim 1, wherein said encapsulate has a matrix composition to shell mass ratio of from about 1:99 to about 90:10.

15. The composition of claim 1, said composition being a consumer product comprising said encapsulate and an adjunct ingredient.

16. A composition according to claim 1, said composition comprising a material selected from
a) an anionic surfactant and/or a nonionic,
b) a solvent;
c) water,
d) an external structuring system
e) optionally one or more materials selected from the group consisting of:
(i) a bleach compatible clay clean polymer,
(ii) a brightener,
(iii) a builder,
(iv) a chelant.

17. A method of treating and/or cleaning a situs, said method comprising
a) optionally washing and/or rinsing said situs;
b) contacting said situs with a composition according to any preceding claim; and
c) optionally washing and/or rinsing said situs.

18. A situs treated with a composition according to claim 1.

* * * * *